United States Patent
Regula

(10) Patent No.: US 6,216,698 B1
(45) Date of Patent: Apr. 17, 2001

(54) FLEXIBLE PESSARY

(75) Inventor: Stanley Regula, Morton Grove, IL (US)

(73) Assignee: Milex Products, Inc., Chicago, IL (US)

(*) Notice: Subject to any disclaimer, the term of this patent is extended or adjusted under 35 U.S.C. 154(b) by 0 days.

(21) Appl. No.: 09/250,582

(22) Filed: Feb. 16, 1999

(51) Int. Cl.7 ..................................................... A61F 6/06
(52) U.S. Cl. ......................................... 128/830; 128/834
(58) Field of Search ..................................... 128/830–841

(56) References Cited

U.S. PATENT DOCUMENTS

| | | | |
|---|---|---|---|
| 40,949 | * 12/1863 | Scattergood | 128/834 |
| 1,083,721 | * 1/1914 | Asch | 128/834 |
| 4,031,886 | 6/1977 | Morhenn . | |
| 4,307,716 | 12/1981 | Davis . | |
| 4,516,570 | 5/1985 | Taban . | |
| 4,579,110 | 4/1986 | Hamou . | |
| 4,607,630 | 8/1986 | Spits . | |
| 4,724,832 | 2/1988 | Strubel et al. . | |
| 4,823,814 | 4/1989 | Drogendijk et al. . | |
| 5,014,722 | 5/1991 | Bauer . | |
| 5,224,494 | 7/1993 | Enhorning . | |
| 5,224,495 | 7/1993 | Robinson . | |

* cited by examiner

Primary Examiner—Michael A. Brown
(74) Attorney, Agent, or Firm—Wallenstein & Wagner, Ltd.

(57) ABSTRACT

An improved pessary, comprising a frame made of an elongated material of generally circular cross-section. This elongated material is then formed into a closed figure of a generally rectangular shape. The frame is then formed into a configuration which has a generally horseshoe shape, in side view. The frame comprises four arms, including a first, second, third, and fourth arm. With the frame in its initial rectangular shape, the first and second arms are generally parallel to each other. In this initial rectangular shape, the third and fourth arms are also generally parallel to each other. In addition, these third and fourth arms are generally perpendicular to the first and second arms. The first and second arms include springs that are crimped onto each of the first and second arms at a position generally in the middle of each of the first and second arms. The springs permit flexing of the first and second arms. The third and fourth arms include springs crimped onto each of the third and fourth arms, at a position generally in the middle of each of the third and fourth arms. These springs also permit flexing of the third and fourth arms. The frame is totally enclosed within a thin and flexible biocompatible material. The biocompatible material is preferably selected from the group including silicone, rubber, or polyvinylchloride.

10 Claims, 1 Drawing Sheet

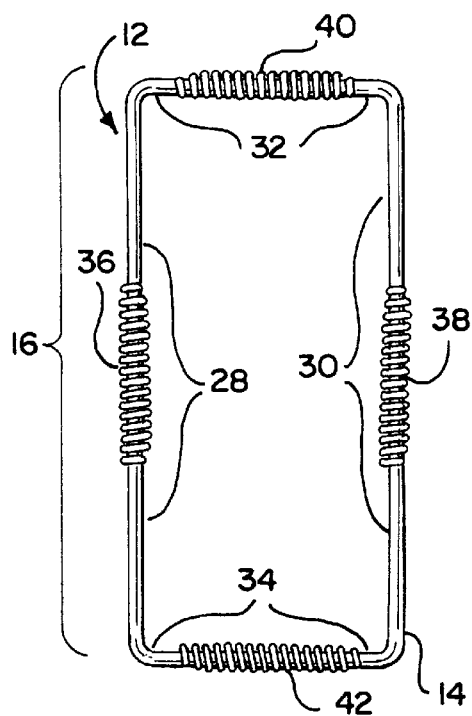
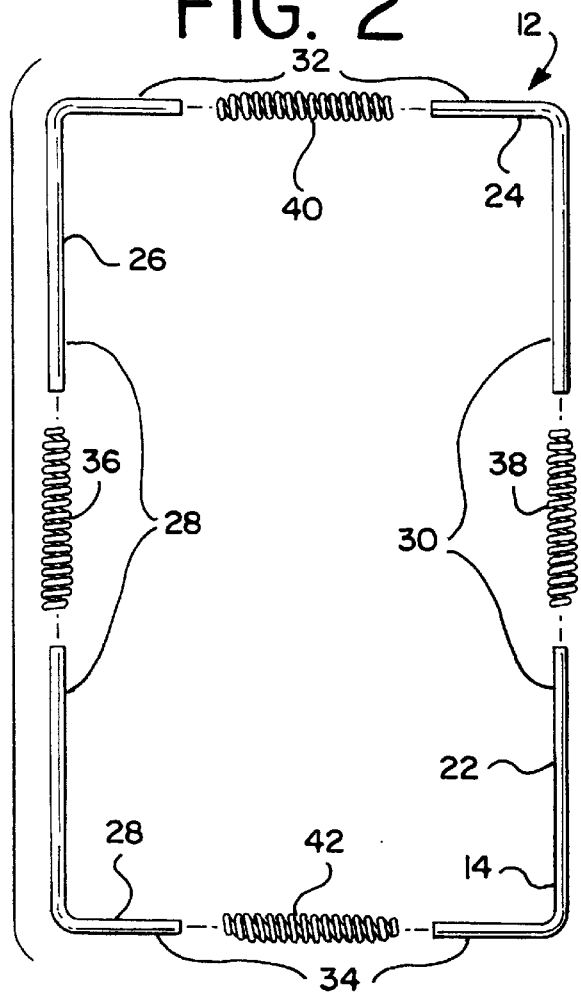
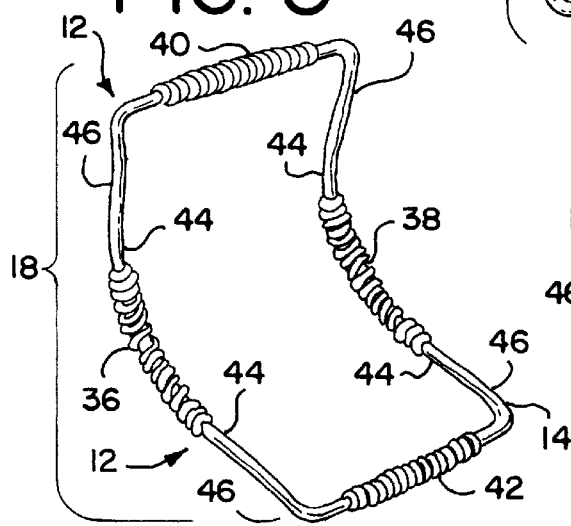
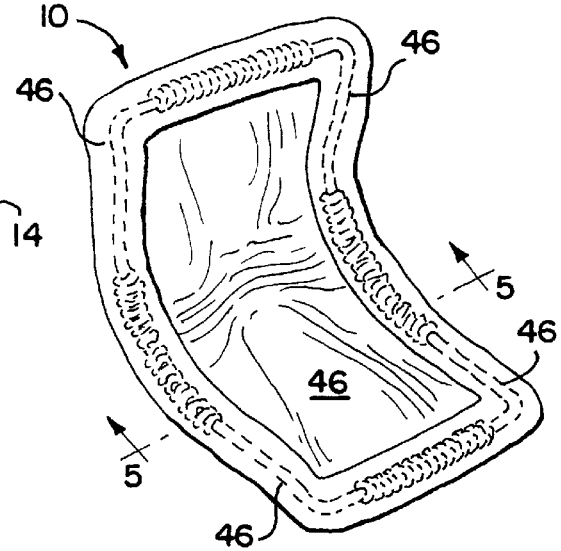
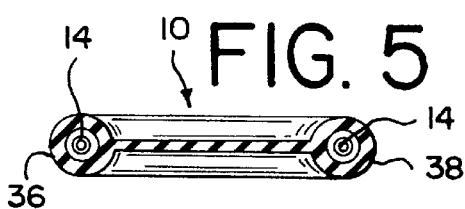

FLEXIBLE PESSARY

TECHNICAL FIELD

This invention relates generally to an improved pessary for effective support of a cystocele, or rectocele, or prolapse, or a combination of geritourinary abnormalities. The improved pessary is preferably of a generally horseshoe shape, and is capable of being reshaped by intrauterine forces while in place within the uterus. The pessary is comprised of a frame completely enclosed by an inert material, such as a silicone. This reshapability of the pessary while in the uterus is the result of placing a flexible segment, such as a spring-type means, along the two central arms of the frame.

BACKGROUND OF THE INVENTION

Various devices, generally known as pessaries, are utilized for the treatment of prolapse of internal female organs, including the organs of the digestive tract and sex organs. Increased age is a risk factor for women for uterine or other prolapse. The use of pessaries is indicated where the correction of prolapse by surgery is inadvisable, as for example where a woman is in generally poor physical condition, or where she is of advanced age.

The first known pessaries are believed to have been small oranges, and may have been in use since 2,000 years ago. Modem literature describing pessaries dates back to a period prior to the 1850's. More recent patents of interest and relating to pessaries include U.S. Pat. Nos. 4,031,886, 4,307,716, 4,516,570, 4,579,110, 4,607,630, 4,724,832, 4,823,814, 5,014,722, 5,224,494, and 5,224,495. The pessaries shown in these patents and otherwise known in the prior art can be of many shapes, including ring shaped, spherical, horseshoe, helical, cylindrical, and ovoid, among others. The inner part of the pessary generally includes a structural support. Such a support may be mechanical, such as a metal frame, or pneumatic, i.e., air supported. The outside surface of the pessary is generally made of an inert, biocompatible material, such as rubber or silicone. A pessary of the horseshoe type is known as a "Gehrung" pessary. One example of such a "Gehrung" pessary is shown at page 14 of a catalog by Milex Products, Incorporated, the assignee of the present application.

The prior art "Gehrung" pessaries provide generally effective support in cases of cystocele and rectocele. The solid metal frame of these prior art devices permits these devices to be bent somewhat into a new shape more precisely meeting the needs of a particular patient. In addition, a lesser flexing of the frame, to an extent that does not permanently change the shape of the device, facilitates insertion.

After insertion into the patient, the shape of these devices does not change, but remains identical to that shape into which it the supporting frame was bent, i.e., the shape just prior to insertion. This tendency to resist changes in shape is generally advantageous for some patients, particularly those patients whose anatomy or general physical conditions do not worsen over time.

However, for those patients whose condition does worsen over time, the convention "Gehrung" pessary may not be ideal. When internal organs undergo further shifts, additional weight and pressure may be placed onto the pessary. As a result of this increased pressure, the pessary may shift within the uterus of the patient. These shifts may in turn increase the pressure on the uterine walls upon which the pessary rests. As a result, a pessary which was comfortable when initially fitted may, at a later time, become uncomfortable for the patient.

SUMMARY OF THE INVENTION

The invention is an improved pessary, comprising a frame made of an elongated material of generally circular cross-section. This elongated material is then formed into a closed figure of a generally rectangular shape. The frame is then formed into a configuration which has a generally horseshoe shape, in side view. The frame comprises four arms, including a first, second, third, and fourth arm. With the frame in its initial rectangular shape, ,the first and second arms are generally parallel to each other. In this initial rectangular shape, the third and fourth arms are also generally parallel to each other. In addition, these third and fourth arms are generally perpendicular to the first and second arms. The first and second arms include flexible segments, such as springs that are crimped onto each of the first and second arms. A preferred, but not mandatory, position for these flexible segments or springs is generally in the middle of each of the first and second arms. The springs permit flexing of the first and second arms.

In another embodiment, the third and fourth arms include flexible segments, such as springs, crimped onto each of the third and fourth arms, at a position preferably, but not necessarily, in the middle of each of the third and fourth arms. These springs also permit flexing of the third and fourth arms.

In general, the frame is totally enclosed within a thin and flexible biocompatible material. The biocompatible material is preferably selected from the group including silicone, rubber, or polyvinylchloride.

BRIEF DESCRIPTION OF THE DRAWINGS

FIG. 1 is a perspective view of the frame made from an elongated material of generally circular cross-section, while that frame is in a flat, generally rectangular shape, and also showing the springs at approximately the mid-points of the arms of the frame;

FIG. 2 is an exploded view of the elongated, rectangular frame of FIG. 1.

FIG. 3 is a perspective view of the frame of FIG. 2, but after it has been formed into a configuration which has a generally horseshoe shape, when viewed in a side view;

FIG. 4 is a perspective view of a pessary in accordance with the invention;

FIG. 5 is a cross-sectional view of a portion of FIG. 4, taken along lines 5—5 of FIG. 4.

DETAILED DESCRIPTION OF THE PREFERRED EMBODIMENT OF THE INVENTION

Components of the invention, and the invention itself, are shown in the accompanying FIGS. 1–5. The invention is an improved "Gehrung" type pessary 10 which provides effective support in cases of cystocele and rectocele. A perspective view of the pessary 10 is shown in FIG. 4, and a portion of that pessary 10 in cross-section is shown in FIG. 5. One example of a frame 12 in accordance with the invention which supports that pessary 10 is shown generally in FIGS. 1, 2, and 3.

The frame 12 provides the pessary 10, when in use, with the rigid structural support necessary to support the weight of organs which will ultimately rest upon it. The basic portion of the frame 12 which is somewhat similar to that used in prior art "Gehrung" pessaries is the elongated material 14 of generally circular cross-section This elongated material 14 of generally circular cross section (see especially FIG. 5) comprises a wire made of a metallic or other rigid material, such as stainless steel, malleable steel, or some other suitable and similar metal. An appropriate wire 14 is a stainless steel wire obtained from Casey Spring Company, Harwood Heights, Ill. 60656, and available as Type 304. This wire has a diameter of 0.072 inch.

As may best be seen in FIG. 1, this stainless steel wire 14 is initially formed into a closed FIG. 16 of a generally rectangular shape. Preferably, as may best be seen in FIG. 2, an exploded view of the frame 12 of FIG. 1, there are four separate wire segments 20, 22, 24, and 26 that form the basic structural portion of this frame 12. The use of four separate wire segments 20, 22, 24, and 26, when joined together with flexible segments, such as for example springs, enables the pessary 10 to flex in a manner to be described below, and in a manner not shown or described in any of the known prior art "Gehrung" pessaries.

When assembled, as may be seen in FIG. 1, the frame 12 comprises four arms, including a first 28, a second 30, a third 32, and a fourth arm 34.

The first arm 28 is made of the vertical portions of wire segments 26 and 20. The second arm 30 is made of the vertical portions of wire segments 22 and 24. The third arm 32 is made of the horizontal portions of wire segments 24 and 26. The fourth arm 34 is made of the horizontal portions of wire segments 22 and 20.

With the frame 10 in its initial rectangular shape 16, as may be seen in FIG. 1, the first 28 and second arms 30 are generally parallel to each other. In this initial rectangular shape 16, the third 32 and fourth arms 34 are also generally parallel to each other. In addition, these third 32 and fourth arms 34 are generally perpendicular to the first 28 and second arms 30.

The first 28 and second arms 30 include a flexible segment, such as springs 36, 38. The flexible segments could be any material which permits flexing of the first 28 and second arms 30, such as a flexible rubber link. These springs 36 and 38 are securely crimped, at their opposite lateral ends, onto each of the first 28 and second arms 30, respectively. While FIGS. 1–5 show these springs 36 and 38 in their preferred position, i.e., at a position generally in the middle of each of the first 28 and second arms 30, the springs 36 and 38 can be at other positions along the first 28 and second arms 30. Moreover, there can be more than one spring secured to and along the first 28 and second arms 30. Springs 36 and 38 can be of various spring tensions, according to the needs of the patient. Springs 36 and 38 are obtained from Casey Spring Company, Harwood Heights, Ill. 60656 as Part No. 1008/1010. The wire used for the springs 36 and 38 has a diameter of approximately 0.0346".

The springs 36 and 38 permit flexing of the first 28 and second arms 30, respectively. This flexing of the first 28 and second arms 30 facilitates insertion and especially permits flexing of the pessary 10 in utero, helping to relieve the pressure on the uterine or other internal walls upon which the pessary 10 rests. As a result, this type of pessary 10 will be comfortable when initially fitted, and will remain comfortable for the patient even in the event of shifts in the internal organs of that patient.

Similarly, as may be seen in FIGS. 1–3, the third 32 and fourth arms 34 include springs 40 and 42, respectively, crimped onto each of the third 32 and fourth arms 34. These springs 40 and 42 are also preferably positioned near the middle of each of the third 32 and fourth arms 34. These springs 40 and 42 also permit flexing of the third 32 and fourth arms 34, again to facilitate insertion and to enhance comfort. As with the first 28 and second arms 30, the third 32 and fourth arms 34 may have more than one spring.

After assembly of the frame 12 and springs 36, 38, 40, and 42 to the configuration of FIG. 1, the frame 12 is then reformed into a configuration 18 which has a generally horseshoe shape, when viewed in side view. In order to help achieve this general horseshoe shape 18, as may best be seen in FIG. 3, portions of the first 28 and second arms 30 of the frame 12 are bent somewhat, at bend points 44 on the first arm 28 and second arm 30. This bending of the frame 12 also enhances the ability of the pessary 10 to conform to the body of the user when in place in utero.

As may also be seen in FIGS. 3 and 4, the respective ends 46 of first arm 28 and second arm 30 are flared outwardly. This slight flaring of the ends 46 of these arms 28 and 30 enhances the ability of the pessary 10 to spread upon flexing of the springs 36 and 38.

In general, the frame 12 is totally enclosed within a thin and flexible biocompatible material 46. The biocompatible material 46 is preferably selected from the group including silicone, rubber, or polyvinylchloride. The biocompatible material 46 is placed onto the frame 12 by known methods, such as insert molding. According to this method, silicone or another biocompatible material 46 is molded onto the fixed, horseshoe shaped frame 18. A preferred biocompatible material 46 is obtained from Shincor Silicones, Inc., 1030 Evans Avenue, Akron, Ohio 44305, and is available as Catalog No. 1950–60.

In another embodiment of the improved pessary (not shown), the pessary may include a frame made of an elongated material, similar to the material that is shown in the FIGURES. In this embodiment, the closed figure is of a generally oval shape. The frame is configured into a generally horseshoe shape, in side view, and the elongated material includes springs or other flexible segments to permit flexing of the elongated material.

Specific embodiments have been illustrated and described. Numerous modifications are possible, which modifications do not significantly depart from the spirit of the invention. Protection is only limited by the scope of the accompanying claims.

What I claim is:

1. An improved organ support device, comprising: a frame made of an elongated material of generally circular cross-section, said material being formed into a closed figure of generally rectangular shape, said frame being configured into a generally horseshoe shape in side view, said frame comprising four arms, including a first, second, third, and fourth arm, said first and second arms being generally parallel to each other, and said third and fourth arms being generally parallel to each other, and said third and fourth arms further being generally perpendicular to said first and second arms, said first and second arms including a flexible segment along said first and second arms, said flexible segment permitting flexing of said first and second arms.

2. The organ support device of claim 1, wherein said third and fourth arms include a flexible segment along each of said third and fourth arms, said flexible segment permitting flexing of said third and fourth arms.

3. The organ support device of claim 1, wherein said frame is totally enclosed within a thin and flexible biocompatible material.

4. The organ support device of claim 3, wherein said biocompatible material is selected from the group including silicone, rubber, or polyvinylchloride.

5. The organ support device of claim 1, wherein the ends of the first and second arms of the frame are bent outwardly.

6. The organ support device of claim 1, wherein said flexible segments comprise springs.

7. The organ support device of claim 1, wherein said flexible segments are placed at a position generally in the middle of each of said first and second arms.

8. An improved organ support device, comprising a frame made of an elongated material, said material being formed into a closed figure, said frame being configured into a generally horseshoe shape in side view, said frame comprising four arms, including a first, second, third, and fourth arm, said first and second arms being generally parallel to each other, and said third and fourth arms being generally parallel to each other, and said third and fourth arms further being generally perpendicular to said first and second arms, said first and second arms including flexible segments positioned along each of said first and second arms, said flexible segments permitting flexing of said first and second arms.

9. The improved organ support device of claim 8, wherein said flexible segments are springs positioned on said first and second arms at a position generally in the middle of each of said first and second arms.

10. The improved organ support device of claim 8, wherein said flexible segment is made of a flexible rubber or plastic material.

* * * * *